United States Patent [19]
Weissman et al.

[11] Patent Number: 6,150,112
[45] Date of Patent: Nov. 21, 2000

[54] METHODS FOR IDENTIFYING DNA SEQUENCES FOR USE IN COMPARISON OF DNA SAMPLES BY THEIR LACK OF POLYMORPHISM USING Y SHAPE ADAPTORS

[75] Inventors: Sherman Weissman, New Haven; Roger Lasken, Guilford, both of Conn.

[73] Assignees: Yale University, New Haven; Molecular Staging Inc., Guilford, both of Conn.

[21] Appl. No.: 09/398,215

[22] Filed: Sep. 17, 1999

Related U.S. Application Data

[60] Provisional application No. 60/100,935, Sep. 18, 1998.
[51] Int. Cl.[7] ............................... C12Q 1/68; C07H 21/02
[52] U.S. Cl. ........................... 435/6; 435/91.1; 435/91.2; 536/23.1; 536/24.2
[58] Field of Search ........................... 435/6, 91.1, 91.2; 536/23.1, 24.2

[56] References Cited

U.S. PATENT DOCUMENTS 5,556,750  9/1996  Modrich et al. ............................. 435/6

OTHER PUBLICATIONS

Straus et al "Genomic subtraction for cloning DNA corresponding to delection mutations" Proc. Natl. Acad. Sci. vol. 87, pp. 1889–1893, Mar. 1990.

McAllister et al "ERnrichment for Loci Identical–by Descent between pairs of Mouse or Human genomes by Genomic Mismatch Scanning" Genomics,vol. 47, pp. 7–11, Jan. 1998.

Riley et al "A novel, rapid method for the isolation of terminal sequences from YAC clones" Nucleic Acid Research, vol. 18, No.10, pp. 2887–2890, 1990.

Cheung et al "Genomic Mismatch Scanning: Applications to linkage and linkage disequilibrium analysis" Am. J. of Human Genetics, vol. 61, No. 4, Suppl. pp. A271, Oct. 1997.

Nelson, Nature Geneticcs (1993), vol. 4: 11–18.

Prasher & Weissman Proc. Nat. Acad. USA (1996)93: 659–663.

Geung et al. Nature Genetics (1998), 18: 225–230.

*Primary Examiner*—Jeffrey Fredman
*Assistant Examiner*—Jeanine Enewold
*Attorney, Agent, or Firm*—Banner & Witcoff, Ltd.

[57] ABSTRACT

A general method for screening genomic or cDNA, or fragments and mixtures thereof, involves sample simplification by the generation of subsets and then subjecting the subsets to a modified mismatch scanning procedure that eliminates DNA having single stranded breaks after a MutSLH cleavage. The methods are particularly useful in human population isolates, including identification of identical-by-descent sequences, genomic comparisons of two or more individuals, and genomic comparisons of two populations of individuals, for the identification of sequences of low polymorphism.

20 Claims, 3 Drawing Sheets

FIG. 1(F)
PERFECTLY MATCHED HETEROHYBRID
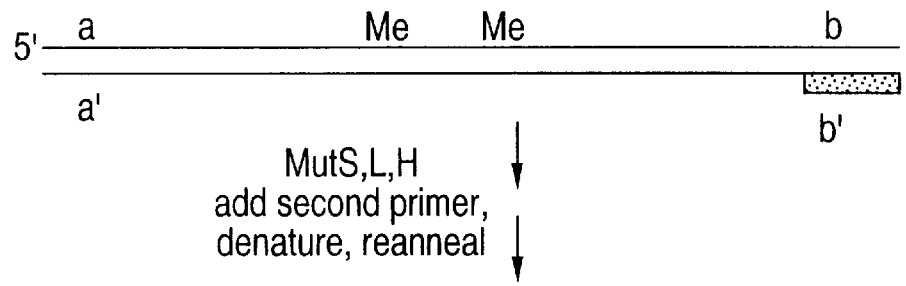
FIG. 1(G)
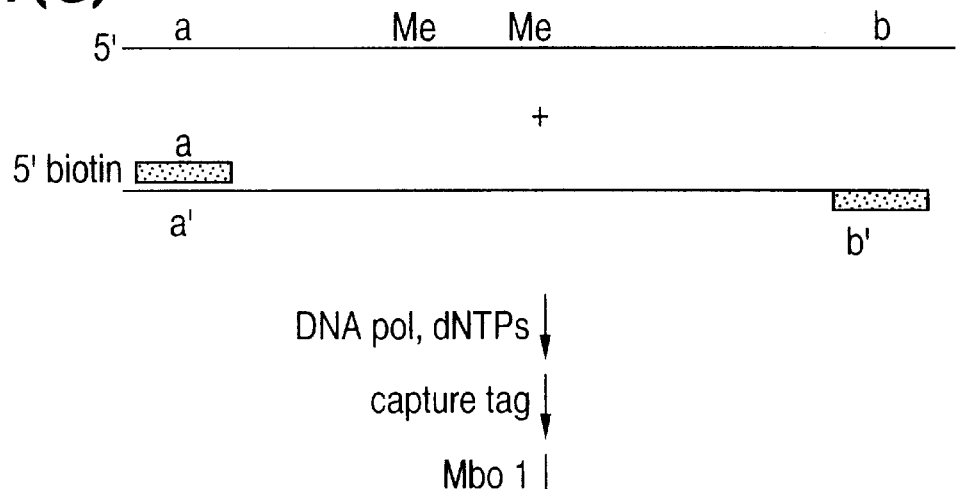
FIG. 1(H)
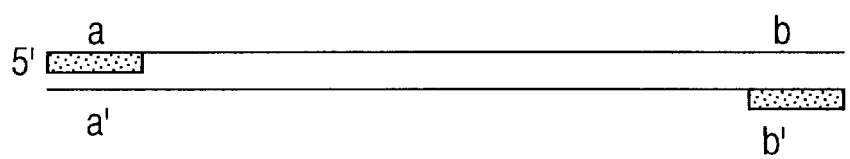
FIG. 1(I)
AMPLIFICATION IS SUCCESSFUL

MISMATCHED HETEROHYBRID

↓ add second primer, denature, reanneal

↓ DNA pol, dNTPs
↓ capture tag
↓ Mbo 1

PCR with both primers ↓  5' ▬▬ a   b' ▬▬ 5'

NO AMPLIFICATION

METHODS FOR IDENTIFYING DNA SEQUENCES FOR USE IN COMPARISON OF DNA SAMPLES BY THEIR LACK OF POLYMORPHISM USING Y SHAPE ADAPTORS

This invention claims the benefit of provisional application Ser. No. 60/100,935 filed Sep. 18, 1998 now abandoned.

TECHNICAL FIELD OF THE INVENTION

This invention relates to methods of genetic mismatch analysis that takes advantage of almost all polymorphisms in the genome and at the same time gives something like a haplotype analysis. The methods are particularly useful in the analysis of population isolates and provides probes or clones of sequences of low polymorphism in two or more samples.

BACKGROUND OF THE INVENTION

In 1993 Nelson and associates described a "genomic mismatch scanning" (GMS) method to directly identify identical-by-descent (IBD) sequences in yeast (Nelson, S. F., et al., *Nature Genetics*, 1993, 4:11–18; this and other papers cited herein are expressly incorporated in their entireties by reference). The method allows DNA fragments from IBD regions between two relatives to be isolated based on their ability to form mismatch-free hybrid molecules. The method consists of digesting DNA fragments from two sources with a restriction endonuclease that produces protruding 3'-ends. The protruding 3'-ends provide some protection from exonuclease III (Exo III), which is used in later steps. The two sources are distinguished by methylating the DNA from only one source. Molecules from both sources are denatured and reannealed, resulting in the formation of four types of duplex molecules: homohybrids formed from strands derived from the same source and heterohybrids consisting of DNA strands from different sources. Heterohybrids can either be mismatch-free or contain base-pair mismatches, depending on the extent of identity of homologous regions.

Homohybrids are distinguished from heterohybrids by use of restriction endonucleases that cleave fully methylated or unmethylated GATC sites. Homohybrids are cleaved into smaller duplex molecules. Heterohybrids containing a mismatch are distinguished from mismatch-free molecules by use of the *E. coli* methyl-directed mismatch repair system. The combination of three proteins of the methyl-directed mismatch repair system MutS, MutL, and MutH (herein collectively called MutSLH) along with ATP introduce a single-strand nick on the unmethylated strand at GATC sites in duplexes that contain a mismatch. Heterohybrids that do not contain a mismatch are not nicked. All molecules are then subject to digestion by Exo III, which can initiate digestion at a nick, a blunt end, or a recessed 3'-end, to produce single-stranded gaps. Only mismatch-free heterohybrids are not subject to attack by Exo III; all other molecules have single-stranded gaps introduced by the enzyme. Molecules with single-stranded regions are removed by absorption to benzoylated napthoylated DEAE cellulose. The remaining molecules consist of mismatch-free heterohybrids which may represent regions of IBD.

Nelson, et al., used *S. cerevisiae* hybrids as a model system and showed that sequences shared by two independently generated hybrids from the same parent strains could be identified in many instances. Experiments of this kind are much easier to do in yeast than humans. The yeast genome is 250 times simpler than the human genome, it contains far fewer repetitive sequences, and genomic sequences of two yeast strains differ more than genomes of unrelated humans. It has thus far not been possible to do comparable experiments with human genomic DNA. In order to do so one needs to use methods to reproducibly generate simplified but highly polymorphic representations of the human genome. Pooling techniques based on mathematical principles are also essential to identify IBD sequences as well as other sequences showing AFD.

The human genome is enormously long, at $3 \times 10^9$ base pairs, and it is far too complex for efficient reannealing of homologous DNA strands after denaturation. The rate of annealing of a mixture of nucleic acid fragments in liquid phase is inversely proportional to their complexity. Efforts have therefore been made to generate simplified representations of the genome for genetic methods based on cross hybridization of homologous sequences from different genomes. The exact degree of simplification of human genomic DNA needed to achieve efficient annealing depends on the conditions of hybridization including total DNA concentration, hybridization buffer, and temperature. In general a 10–100 fold simplification is needed for efficient annealing to occur at high DNA concentrations in high salt aqueous solutions (Lisitsyn, N. A., et al., *Science*, 1993, 259:946–951).

It would be useful to have superior ways of analyzing human DNA.

SUMMARY OF THE INVENTION

It is an object of the invention to provide methods for simplifying DNA analyses, particularly analyses of human genomic DNA and DNA fragments.

It is a further and more specific object of the invention to provide a genomic mismatch scheme that simplifies genomic DNA analysis by dividing DNA into subsets before reannealing and eliminating DNA with single-stranded breaks after MutSLH cleavage.

These and other objectives of the invention are accomplished by the present invention, which provides methods for comparing two or more DNA samples to identify sequences of low polymorphism by processing and reannealing the samples to obtain hemimethylated DNA subsets, and selectively amplifying perfectly matched heterohybrids. In a typical embodiment, pooled DNA samples are subjected to a sequence of steps including (a) methylating the DNA, and cutting the methylated DNA with an enzyme that makes infrequent cuts such as PvuI to obtain fragments; (b) ligating Y-shaped adapters to the fragments to obtain fragment-plus-adapter constructs; (c) carrying out a single primer extension reaction in the presence of a primer complementary to at least a portion of the adapter at the 3'-end of the fragment-plus-adapter constructs and extending across the adapter ligation site, and having at least one nucleotide overlap into the DNA fragment sequence, a tag such as biotin at the 5'-end, and a GATC site at least about 6 nucleotides from the tag to obtain hemimethylated fragment-plus-adapter constructs; (d) trapping the hemimethylated DNAs obtained in step (c) with a capture agent such as, where biotin is the tag, avidin or strepavidin that binds to the tag and then cleaving the tag from the trapped DNAs, e.g., with MboI; (e) denaturing the hemimethylated DNAs and reannealing them to form heterohybrid duplex DNAs containing a DNA strand obtained from each of two different samples, e.g., individuals; (f) nicking any heterohybrids that contain mismatched base pairs with MutSLH; (g) denaturing the DNAs obtained in step (f) and subjecting the single strands to a second primer extension reaction with the primer being complementary to the 3'-end of the unmethylated fragment strand, having a tag covalently attached to the 5'-end, and containing a GATC sequence sufficiently removed from the 5'-end to allow restriction endonuclease cutting to occur; (h) trapping the duplex DNAs obtained in step (g) with a capture agent that binds the tag, and releasing them with MboI; and either (i) subjecting the trapped duplex DNAs obtained in step (h) to a PCR reaction using primers complementary to the 3'-ends of the heterohybrids obtained in step (e) such that any fragments nicked by MutSLH in step (f) cannot be amplified; or (j) preparing a splint oligonucleotide complementary to the sequences at the 5'- and 3'-end of the full length DNA produced in step (h) for perfectly matched homoduplexes such that annealing of the splint oligonucleotide circularizes the strand, annealing this oligonucleotide to the denatured single strands from step (h), ligating the product with DNA ligase, and incubating the ligated product with a DNA polymerase in the presence of dideoxynucleoside triphosphates to extend the 3'-end of the splint oligonucleotide in a rolling circle DNA amplification; and (k) identifying the products of the PCR reaction or the rolling circle amplification as sequences of low polymorphism. Some variations in steps and in the overall scheme are employed in alternate embodiments. For example, the DCM methylase system can be used for steps (a) through (d) so that the DAM methylase system is available for treatment of a DNA or pool of DNA and subsequent mixing, denaturation, and reannealing with a second, unmethylated DNA or pool of DNA, followed by selection for heterohybrids using the methods described in Nelson, et al., cited above. Methods of the invention can be employed for any type of DNA samples, including genomic IBD sequences and cDNA, and are particularly adapted to comparisons of DNA from two or more individuals or populations of individuals, including those of different ethnicity.

BRIEF DESCRIPTION OF THE DRAWING

The figure is a diagram illustrating DNA process steps used in some embodiments of the invention summarized above and described (with reference to the figure) in greater detail below.

FIG. 1F, Mut S,L,H complex is added to bind mismatches and nick them; duplexes are denatured;

FIG. 1G, a second primer is added to bind to the opposite strand from the first primer;

FIG. 1H, DNA synthesis is carried out, duplexes are captured by means of the tag and released by cutting with a restriction enzyme which cleaves within the primer sequence;

FIG. 1I, released DNA fragments are amplified;

DETAILED DESCRIPTION OF THE INVENTION

This invention provides for the screening of complex DNA preparations, including complex DNA comprised of genomic segments or cDNAs, and the isolation of genes without requiring prior knowledge of their biochemical function or map position. Methods of the invention divide DNA into subsets and then manipulate the subsets using a mismatch repair system and capture techniques to obtain specific DNA sequences, including genomic subsets of long genomic DNA generated by selective amplification of sequences exhibiting low polymorphism.

As used herein, "polymorphism" refers to genetic sequence variation between different individuals of a species. A "homoduplex" is double-stranded DNA where both strands derive from the same genome or pools of genome samples, and a "heteroduplex" is double-stranded DNA where each strand originated from different genomes or different pools of genomes. By "perfectly matched" is meant double-stranded DNA where each base residue is correctly paired with a base on the opposite strand, i.e., A to T and C to G. By "mismatched" is meant double-stranded DNA where at least one base residue on either strand is either not paired with any residue, or paired with an incorrect base, i.e., A not paired with T, C not paired with G.

In a typical practice of a method of the invention, at least one DNA sample is methylated, usually at the GATC sites with bacterial DAM methylase, and the sample is then cut with an enzyme that makes infrequent cuts such as PvuI. Any type of DNA sample may be subjected to methods of the invention, including genomic DNA, genomic fragments, cDNA, cDNA fragments, and mixtures of any of these. It is an advantage of the invention that it can be used to identify identical-by-descent sequences of low polymorphism in complex human or other genomic DNA samples.

Figure 1A:
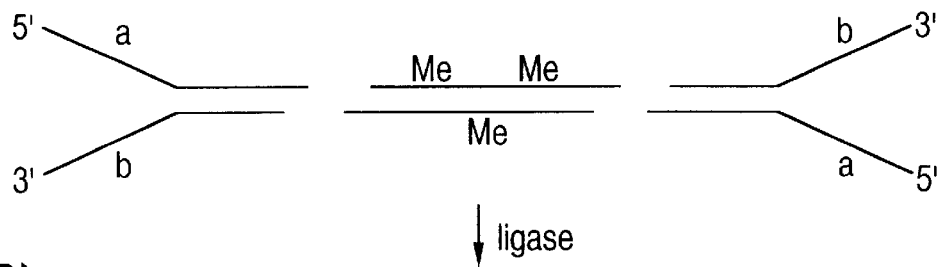
FIG. 1A, Y-shaped adaptors and methylated DNA are shown.
Figure 1B:
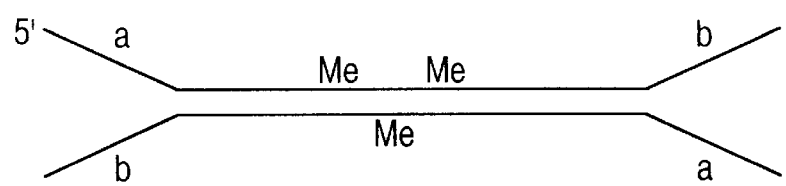
FIG. 1B, the adaptors are ligated to the methylated DNA.

Adapters are then ligated to the fragments to obtain fragment-plus-adapter constructs. Linear or Y-shaped adapters may be employed. Y-shaped adapters are used in many preferred embodiments, but in some cases where Y-shaped adapters are illustrated, the methods can also be adapted to conventional linear adapters. Y-shaped adapters have been described (see Prashar, Y., and Weissman, S., *Proc. Natl. Acad. Sci. USA*, 1996, 93:659–663). A Y-shaped adapter typically has an overhang on its 3' end for ligation, and on the 5' end it has a stretch of noncomplementary sequence on the opposite strands, giving rise to its Y shape (see FIGS. 1A and B). It is an advantage of the invention that, in preferred embodiments, the Y-shaped adapters allow for the synthesis of non-overlapping subsets of DNA. If the invention is carried out with conventional, linear primers, then the PCR-generated subsets will be partially overlapping, that is, some DNA sequences will be represented in more than one subset.

Figure 1C:
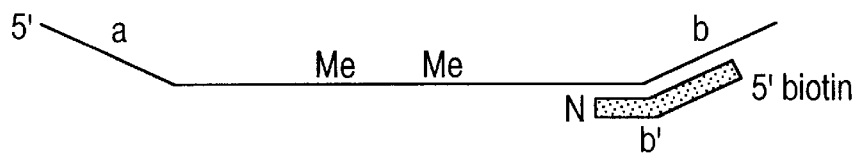
FIG. 1C, a first tagged primer is annealed to the adapter and at least one additional nucleotide.

The fragment-plus adapter constructs are subjected to a single primer extension reaction in the presence of a primer complementary to at least a portion of the adapter at the 3'-end of the fragment-plus-adapter constructs and extending across the adapter ligation, and having at least one nucleotide overlap into the DNA fragment sequence, a tag at the 5'-end, and a GATC site at least about 6 nucleotides from the tag to obtain hemimethylated fragment-plus-adapter constructs. In some embodiments, the annealed primer extends across the adapter ligation site one nucleotide into the DNA fragment sequence; in others, they extend two; and in others more than two. The number of nucleotides and the identity of the nucleotides that the primer extends across the adapter ligation site determines the members of the subset to be replicated. The tag in many embodiments is biotin, illustrated in FIG. 1C. The overall step divides the sample DNA into non-overlapping subsets, and provides duplex DNAs having only one strand methylated, i.e., hemimethylated DNAs.

Figure 1D:
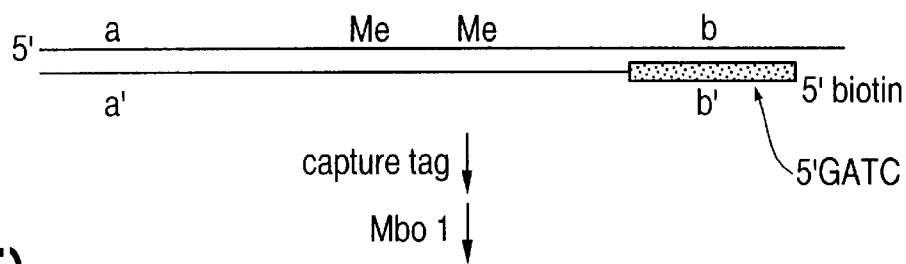
FIG. 1D, the primer is extended to form a double stranded duplex containing a tag.
Figure 1E:
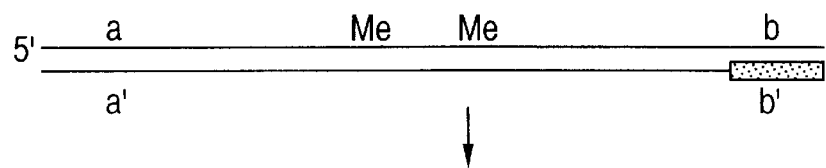
FIG. 1E, the construct is cleaved with an enzyme having a recognition and cleavage site within the primer to release the tag.

Hemimethylated DNAs obtained in the extension reaction are trapped with a capture agent that binds to the tag. In the case of biotin, the capture agent is avidin or strepavidin. The tag is then cleaved off with MboI or another enzyme that poorly cuts the hemimethylated internal fragment. See FIGS. 1D to E.

Figure 1J:
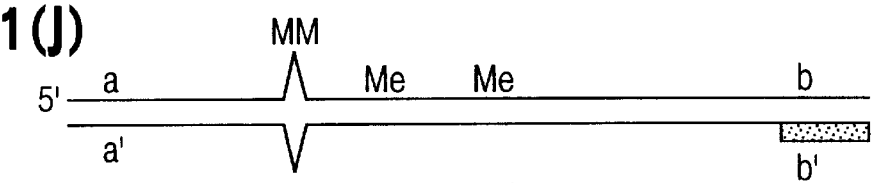
FIG. 1J, mismatched heterohybrids are shown.
Figure 1K:
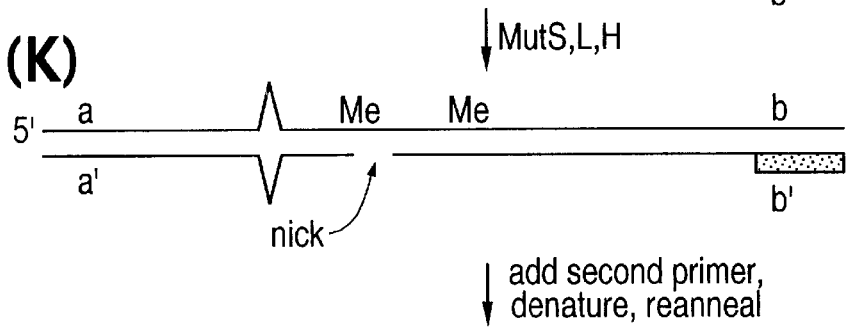
FIG. 1K, heterohybrids are treated with Mut S, L, H complex to nick unmethylated strands at mismatch sites.
Figure 1L:
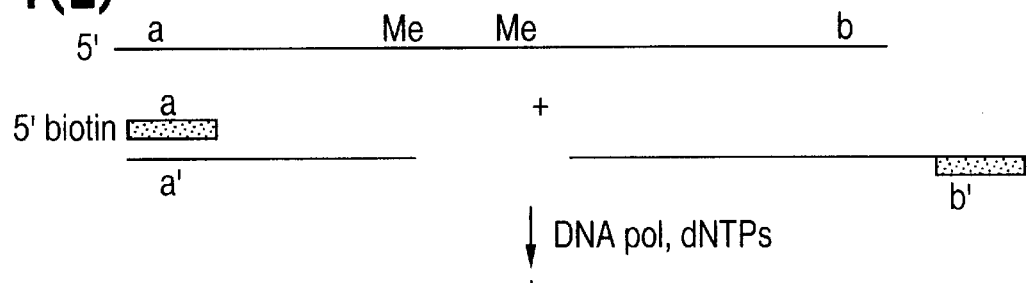
FIG. 1L, a second primer is annealed complementary to the unmethylated strand.
Figure 1M:
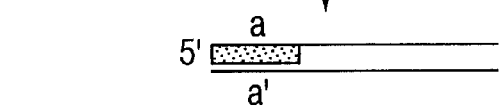
FIG. 1M, DNA synthesis, tag capture, and restriction enzyme cleavage yield a duplex containing only one primer binding site which thus cannot be amplified.

The hemimethylated DNAs are then denatured and reannealed to form heterohybrids which contain a DNA strand from each of two samples, e.g., from two individuals. Where a large number of DNA samples have been pooled together, most of the reannealed duplex DNA will be heterohybrids. The reannealing thus primarily results in perfectly matched heterohybrids (FIG. 1F) or mismatched heterohybrids (FIG. 1J) depending upon the degree of polymorphism. The heterohybrids are then subjected to MutSLH, which nicks any that contain the mismatched base pairs expected for regions of high polymorphism (see U.S. Pat. No. 5,556,750 to Modrich, et al., Cheung, V. G., et al., *Nature Genetics,* 1998, 18:225–230, and the references cited therein).

The DNA obtained after MutSLH treatment are denatured and subjected to a second primer extension reaction with the primer being complementary to the 3'-end of the unmethylated fragment strand, having a tag such as biotin covalently attached to the 5'-end, and containing a GATC sequence sufficiently removed from the 5'-end to allow restriction endonuclease cutting to occur. Duplex DNAs obtained after this step can be captured with a capture agent that binds the tag, i.e., avidin or strepavidin where the tag is biotin, and released with an enzyme such as MboI.

Trapped duplex DNAs can be either amplified in a PCR reaction using primers complementary to the 3'-ends of the heterohybrids obtained in step (e) such that any fragments nicked by MutSLH cannot be amplified; or amplified in a rolling circle amplification of multiple copies (recently reviewed by Hingorani, M. M., and O'Donnell, M., *Current Biology,* 1998, 8:R83–86 and by Kelman, Z., et al., *Structure,* 1998, 6:121–5) after preparing a splint oligonucleotide complementary to the sequences at the 5'- and 3'-end of the full length DNA produced for perfectly matched homoduplexes shown in FIG. 1H such that annealing of the splint oligonucleotide circularizes the strand, annealing this oligonucleotide to the denatured single strands, ligating the product with DNA ligase, and incubating the ligated product with a DNA polymerase in the presence of dideoxynucleoside triphosphates to extend the 3'-end of the splint oligonucleotide in a rolling circle DNA amplification. As used herein, a "polymerase chain reaction" includes conventional PCR, as well as modifications employing betaine, proof-editing polymerases, DMSO, and the like, and combinations thereof. Likewise, "rolling circle amplification" includes variants described by Hingorani and O'Donnell, cited above, and specifically encompasses modifications using a reconstituted bacterial polymerase III system including holoenzyme, helicase, clamp proteins, and clamp loading proteins (Bloom, L. B., et al., *J. Biol. Chem.,* 1997, 272:27919–27930).

As can be seen from FIGS. 1F to I and J to M, only mismatched heterohybrids are cut by MutSLH. Thus, after denaturing, reannealing, duplex formation from single strands, and trapping the duplexes, only perfectly matched heterohybrids give a primer annealing site, and so only perfectly matched heterohybrids are amplified. After MutSLH treatment, DNA with single strand breaks are eliminated. Thus products of the method which are derived from perfectly matched heterohybrids can be identified as sequences of low polymorphism, which include identical-by-descent (IBD) sequences.

There are numerous variations of the overall procedure, and for preparing the probe. Variations in primers having larger overlap with DNA fragments and various amplification techniques have already been mentioned. Following selective isolation of duplex DNA, it could be transcribed with T7 or other appropriate RNA polymerase, and the RNA used as a direct probe, or reconverted into double-stranded DNA.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for comparing at least two DNA samples to identify sequences of low polymorphism comprising:

(a) preparing a DNA sample by methylating GATC sites with bacterial DAM methylase, and cutting the methylated DNA with an enzyme that makes infrequent cuts to obtain fragments;

(b) ligating Y-shaped adapters to the fragments to obtain fragment-plus-adapter constructs;

(c) carrying out a single primer extension reaction in the presence of a primer complementary to at least a portion of the adapter at the 3'-end of the fragment-plus-adapter constructs and extending across the 3'-end adapter ligation site, and having at least one nucleotide overlap into the DNA fragment sequence, a tag at the 5'-end, and a GATC site at least about 6 nucleotides from the tag to obtain hemimethylated fragment-plus-adapter constructs;

(d) trapping the hemimethylated DNAs obtained in step (c) with a capture agent that binds to the tag and then cleaving the tag from the trapped DNAs with MboI;

(e) denaturing the hemimethylated DNAs and reannealing them to form heterohybrid duplex DNAs containing a DNA strand obtained from each of two different samples;

(f) nicking any heterohybrids that contain mismatched base pairs with MutSLH;

(g) denaturing the DNAs obtained in step (f) and subjecting the single strands to a second primer extension reaction with the primer being complementary to the 3'-end of the unmethylated fragment strand, having a tag covalently attached to the 5'-end, and containing a GATC sequence sufficiently removed from the 5'-end to allow restriction endonuclease cutting to occur;

(h) trapping the duplex DNAs obtained in step (g) with a capture agent that binds the tag, and releasing them with MboI; and either (i) subjecting the trapped duplex DNAs obtained in step (h) to a PCR reaction using primers complementary to the 3'-ends of the heterohybrids obtained in step (e) such that any fragments nicked by MutSLH in step (f) cannot be amplified; or (j) preparing a splint oligonucleotide complementary to the sequences at the 5'- and 3'-end of the full length DNA produced in step (h) for perfectly matched homo-duplexes shown in FIG. 1H such that annealing of the splint oligonucleotide circularizes the strand, annealing this oligonucleotide to the denatured single strands from step (h), ligating the product with DNA ligase, and incubating the ligated product with a DNA polymerase in the presence of dideoxynucleoside triphosphates to extend the 3'-end of the splint oligonucleotide in a rolling circle DNA amplification; and (k) identifying the products of the PCR reaction or the rolling circle amplification as sequences of low polymorphism.

2. A method according to claim 1 wherein the DNA samples are genomic DNA, genomic DNA fragments, or mixtures thereof.

3. A method according to claim 2 wherein the DNA sequences identified are genomic identical-by-descent (IBD) sequences.

4. A method according to claim 1 wherein the tags are biotin and the capture agents are avidin or strepavidin.

5. A method according to claim 1 wherein the primers employed in preparing the primer-plus-adapter constructs of step (b) extend across the adapter ligation site one nucleotide into the DNA fragment sequence.

6. A method according to claim 1 wherein the primers employed in preparing the primer plus adapter constructs of step (b) extend across the adapter ligation site two nucleotides into the DNA fragment sequence.

7. A method according to claim 1 wherein the samples are cDNA.

8. A method for identifying genomic DNA sequences that can be used to compare at least two DNA samples for sequences of low polymorphism comprising:

(a) preparing genomic DNA samples by methylating GATC sites with bacterial DAM methylase and cutting the methylated DNA with an enzyme that makes infrequent cuts to obtain fragments;

(b) ligating Y-shaped adapters capable of binding to ends of the fragments obtained in step (a) to obtain fragment-plus-adapter constructs using primers that extend across the adapter ligation site one or two nucleotides into the fragments;

(c) carrying out a single primer extension reaction in the presence of a primer complementary to at least a portion of the adapter at the 3'-end of the fragment-plus-adapter constructs and extending across the 3'-end adapter ligation site, and having a two nucleotide overlap into the DNA fragment sequence, biotin at the 5'-end, and a GATC site at least about 6 nucleotides from the tag to obtain hemimethylated fragment-plus-adapter constructs;

(d) trapping the hemimethylated, biotinylated DNAs obtained in step (c) with avidin or strepavidin and then cleaving the biotin from the trapped DNAs with MboI;

(e) denaturing the hemimethylated DNAs and reannealing them to form heterohybrid duplex DNAs containing a DNA strand obtained from each of two different samples;

(f) nicking any heterohybrids that contain mismatched base pairs with MutSLH;

(g) denaturing the cut DNAs obtained in step (f) and subjecting the single strands to a second primer extension reaction with the primer being complementary to the 3'-end of the unmethylated fragment strand, having a tag covalently attached to the 5'-end, and containing a GATC sequence at least about 6 nucleotides from the 5'-end;

(h) trapping the duplex DNAs obtained in step (g) with avidin or strepavidin and releasing them with MboI;

(i) subjecting the trapped duplex DNAs obtained in step (h) to a PCR reaction in the presence of unlabelled bases and primers complementary to the 3'-ends of the heterohybrids obtained in step (e) such that any fragments nicked by MutSLH in step (f) cannot be amplified; and (j) using the products of the PCR reaction in identifying sequences of low polymorphism.

9. A method according to claim 8 wherein the DNA sequences identified are genomic identical-by-descent sequences.

10. A method according to any of claims 1 to 9 wherein the Y-shaped adapters ligated to the fragments have a stretch of noncomplementary sequences on one end and a stretch of complementary sequences on the other end capable of ligation to the fragment such that ligation of the adapters to both ends of the fragment results in a fragment-plus-adapter construct having the Y-shaped structure at each end with the same single-stranded DNA sequence present and both 3'-ends and the same single-stranded sequence present at both 5'-ends.

11. A method according to claim 10 wherein the primers employed in preparing the fragment-plus-adapter constructs of step (b) extend across the adapter ligation site one nucleotide into the DNA fragment sequence.

12. A method according to claim 10 wherein the primers employed in preparing the fragment-plus-adapter constructs of step (b) extend across the adapter ligation site two nucleotides into the DNA fragment sequence.

13. A method according to claim 1 or 7 wherein the enzyme that makes infrequent cuts in step (a) is PvuI.

14. A method for identifying genomic DNA sequences as identical-by-descent that can be used to compare at least two DNA samples for sequences of low polymorphism comprising:

(a) preparing genomic DNA samples by methylating GATC sites with bacterial DAM methylase and cutting the methylated DNA with PvuI;

(b) ligating Y-shaped adapters capable of binding to ends of the fragments obtained in step (a) to obtain fragment-plus-adapter constructs that extend one nucleotide into the fragment sequence;

(c) carrying out a single primer extension reaction in the presence of a primer complementary to a portion or the entire sequence of the adapter at the 3'-end of the fragment-plus-adapter constructs and extending across the adapter ligation site, and having a two nucleotide overlap into the DNA fragment sequence, biotin at the 5'-end, and a GATC site at least about 6 nucleotides from the biotin to obtain hemimethylated fragment-plus-adapter constructs;

(d) trapping the hemimethylated DNAs obtained in step (c) with strepavidin and then cleaving the tag from the trapped DNAs with MboI;

(e) denaturing the hemimethylated DNAs and reannealing them to form heterohybrid duplex DNAs containing a DNA strand obtained from each of two different samples;

(f) nicking any heterohybrids that contain mismatched base pairs with MutSLH;

(g) denaturing the cut DNAs obtained in step (f) and subjecting the single strands to a second primer extension reaction with the primer being complementary to the 3'-end of the unmethylated fragment strand, having biotin covalently attached to the 5'-end, and containing a GATC sequence at least about 6 nucleotides from the 5'-end;

(h) trapping the duplex DNAs obtained in step (g) with strepavidin, and releasing them with MboI;

(i) subjecting the trapped duplex DNAs obtained in step (h) to a PCR reaction in the presence of unlabelled bases and primers complementary to the 3'-ends of the heterohybrids obtained in step (e) such that any fragments nicked by MutSLH in step (f) cannot be amplified; and (j) using the products of the PCR reaction in identifying sequences of low polymorphism.

15. A method according to any of claims 1 to 6, 8, 9, 11, 12 or 14 wherein the DNA samples are obtained from two or more individuals.

16. A method according to claim 15 wherein the individuals are of different ethnicity.

17. A method according to claim 15 wherein the DNA samples are obtained from two individuals.

18. A method according to any of claims 1 to 6, 8, 9, 11, 12, or 14 wherein the DNA samples are obtained from two or more populations of individuals.

19. A method according to claim 18 wherein the DNA samples are obtained from two populations of individuals.

20. A method according to claim 14 wherein the strepavidin is attached to beads.

* * * * *